(12) United States Patent
Richardson (10) Patent No.: US 6,331,520 B1
(45) Date of Patent: Dec. 18, 2001

(54) PHARMACEUTICAL COMPOSITIONS OF PEPTIDES HAVING LOW SOLUBILITY IN PHYSIOLOGICAL MEDIUM

(75) Inventor: Peter Richardson, Epsom (GB)

(73) Assignee: Applied Research Systems ARS Holding NV (CH)

( * ) Notice: Subject to any disclaimer, the term of this patent is extended or adjusted under 35 U.S.C. 154(b) by 0 days.

(21) Appl. No.: 09/451,013

(22) Filed: Nov. 29, 1999

Related U.S. Application Data (63) Continuation of application No. PCT/EP98/03079, filed on May 26, 1998.

(30) Foreign Application Priority Data

May 28, 1997 (EP) .................................................. 97108593
Dec. 3, 1997 (EP) .................................................. 97121246

(51) Int. Cl.[7] ........................... C07K 7/23; A61K 38/25; A61K 38/09
(52) U.S. Cl. .............................. 514/2; 530/324; 530/328; 514/12; 514/13; 514/15
(58) Field of Search ...................................... 530/328, 324, 530/313; 514/12, 13, 15

(56) References Cited

U.S. PATENT DOCUMENTS

| | | | |
|---|---|---|---|
| 4,935,491 | * | 6/1990 | Folkers .................................. 530/313 |
| 5,284,657 | * | 2/1994 | Lu et al. .............................. 424/435 |
| 5,382,574 | * | 1/1995 | Jorgensen .................................. 514/3 |
| 5,487,898 | | 1/1996 | Lu et al. . |

FOREIGN PATENT DOCUMENTS

| | | |
|---|---|---|
| 0374120 | 6/1990 | (EP) . |
| 0517211A1 | 12/1992 | (EP) . |
| 377 665 B1 | * 12/1995 | (EP) . |
| 0787497A2 | 8/1997 | (EP) . |
| 9109617 | 7/1991 | (WO) . |

* cited by examiner

Primary Examiner—F. T. Moezie
(74) Attorney, Agent, or Firm—Ostrolenk, Faber, Gerb & Soffen, LLP

(57) ABSTRACT

Pharmaceutical compositions are described, which comprise:
a) a peptide poorly soluble in aqueous physiological saline solution, as active ingredient;
b) a non-ionic aromatic hydrotropic pharmaceutically acceptable agent; and
c) a physiological aqueous solution.

6 Claims, 1 Drawing Sheet

FIGURE 1

PHARMACEUTICAL COMPOSITIONS OF PEPTIDES HAVING LOW SOLUBILITY IN PHYSIOLOGICAL MEDIUM

CROSS-REFERENCE TO RELATED APPLICATIONS

This is a continuation application of International Application PCT/EP98/03079, with an International filing date of May 26, 1998.

FIELD OF THE INVENTION

The present invention relates to a pharmaceutical composition comprising:
 a) a peptide poorly soluble in aqueous physiological saline solution, as active ingredient;
 b) a non-ionic aromatic hydrotropic pharmaceutically acceptable agent; and
 c) a physiological aqueous solution.

According to a preferred embodiment of the invention, the peptide (a) is an LHRH analogue or a GRF peptide.

BACKGROUND OF THE INVENTION

It is often necessary to improve the solubility of a drug in physiological media in order to achieve effective clinical performance of injectable formulations of the drug. Peptide drugs are often poorly soluble in physiological media due to the presence of hydrophobic substituents.

Solubility problems can also lead to poor absorption by other routes of administration and in some cases suitable solubilising agents can aid the absorption of the drug by other routes, for example oral or nasal.

Exemplary peptide drugs that are so poorly soluble in physiological media are LHRH analogues and growth hormone releasing factor (GRF) peptides.

Luteinising hormone releasing hormone (LHRH or GNRH) is a decapeptide secreted by hypothalamus and capable of inducing the release of both LH and FSH. It has the following formula: pyroGlu-His-Trp-Ser-Tyr-Gly-Leu-Arg-Pro-Gly-$NH_2$(SEQ ID No:1).

LHRH can either stimulate pituitary gonadotropin secretion or be a potent inhibitor. When administered in a precise pulsatile pattern LHRH can restore the normal cyclic gonadotropin secretion. Pulsatile administration of LHRH using a computerized pump was used with good results in the induction of ovulation in anovulatory women with hypothalamic dysfunction. When administered chronically, LHRH or its agonists proved to be potent inhibitors of gonadotropic secretion, providing a temporary (fully reversible) gonadotropin specific medical hypophisectomy.

To date, thousands of LHRH analogs have been synthesized, that can act either as agonists or antagonists. In order to produce LHRH antagonists, which work by receptor occupancy, it is necessary to substitute several amino acids on the LHRH molecule. Antagonists also require precise topological features to achieve high binding affinity to the receptor. There are a lot of LHRH analogues recently synthesized, in which the amino acids contain aromatic or other functional groups capable of the so-called hydrotropic interaction. The use of LHRH antagonists with their immediate inhibition of gonadotrophin release may be useful in therapeutic areas, such as contraception and in treatment of hormone-dependent disorders. In the case of hormone-dependent tumors, avoiding the initial stimulatory phase produced by LHRH agonists may be a particular advantage. For a review on LHRH analogues, see Karten and Rivier, 1986.

Antide, in particular, is a potent LHRH antagonist, with formula, biological activity and preparation as described in EP Patent 377,665.

From studies carried out by the Applicant, it resulted, for example, that antide has a very poor solubility in 0.9% NaCl solution (solubility 25 µg/ml) or other isotonic media such as phosphate buffered saline (solubility was 16 µg/ml). Previous aqueous formulations of antide have shown poor bioavailability and pharmacokinetic reproducibility. This is due to antide being present at the site of injection in concentrations above 25 µg/ml for example, which leads to the formation of a precipitate on contact with the physiological medium. This precipitate can be gelatinous in nature and has a detrimental effect on drug absorption, as shown by clinical investigations carried out by the Applicant.

Other gonadotrophin releasing hormone antagonists in aqueous solutions can form gel structures and in addition, the solubility is known to increase as the pH of the solution is reduced, due to increased ionisation of the molecule (Cannon J. B, et al., 1995).

GRF (also called Somatorelin) is a peptide secreted by the hypothalamus which promotes the release of growth hormone from the anterior pituitary. It occurs naturally as 44-, 40-, and 37-amino acid peptides; the 44-amino acids form may possibly be converted into smaller forms, but all are reported to be active, the activity residing in the first 29 amino acid residues. A peptide corresponding to the 1–29 amino acid sequence of human GRF [hGRF(1–29)], also called Sermorelin, has been prepared by recombinant DNA technology as described in European Patent EP 105 759.

Sermorelin has been used in the form of acetate for the diagnosis and treatment of growth hormone deficiency.

GRF has a therapeutic value for the treatment of certain growth-hormone related disorders. The use of GRF to stimulate the release of GH is a physiologic method of inducing long bone growth or protein anabolism.

It is well known that the natural form of GRF can suffer from chemical degradation in aqueous solution, primarily of Asn at position 8 which results in reduced biological potency (Friedman et al., 1991; Bongers et al., 1992).

The main hydrolytic reactions occurring in GRF are sensitive to pH and reported to be: rearrangement of $Asp^3$, at pH 4–6.5, cleavage of the $Asp^3$-$Ala^4$ bond at pH 2.5–4.5, deamidation and rearrangement of $Asn^8$ at pH above 7 (Felix A. M., 1991). Due to the combined degradation pathways, unstabilised aqueous solutions GRF are most stable in the pH range 4–5. Bongers et al. (Bongers et al., 1992) have shown that the deamidation reaction at $Asn^8$ increases rapidly as the pH is raised above pH 3.

Various workers have made analogues of GRF by substitution of amino acids into the natural GRF sequence to improve the chemical stability (Serono Symposia USA, 1996; Friedman, 1991). While modification can be an effective means to improve the stability and retain bioactivity, it may be undesirable due to altered immunogenicity, which could be a problem for chronic therapies such as growth hormone deficiency.

It is known from the literature that, in certain cases, the addition of aromatic agents to solutions of proteins can cause a negative effect on solubility, resulting in precipitation. For example, when aromatic agents were brought into contact with recombinant human growth hormone (rhGH), conformational changes or denaturation occurred, resulting in the formation of rhGH aggregates. (Maa Y. F. and Hsu C. C., 1996). Additionally, to show that this was not a general phenomenon, it was shown that aromatic amino acid derivatives improved the solubility and enhanced the absorption of growth hormone (Leone Bay A, et al., 1996).

Nicotinamide has been reported to solubilise conventional pharmaceutical compounds (i.e. non-peptides with molecular weight less than 1000 daltons) by a process of charge transfer complexation, also called hydrotropic solubilisation. This process may result from the interaction of aromatic groups in the solubilising agent and aromatic or other suitable functional groups on the drug molecule. For example see Rasool et al., 1991.

However, the Applicant has found, and the corresponding data are here reported in the experimental section, that other molecules, containing aromatic groups such as benzoate or salicylate, which could interact by a hydrotropic mechanism (Jain N. K. and Patel V. V., 1986), show only a minor improvement in the solubilisation of an LHRH analogue (antide) in saline solution.

European Patent Application 0 649 655 describes the solubilisation of a water insoluble anti-ulcer drug using nicotinamide in order to produce a useful injectable form. Many potential derivatives of the active moiety are claimed, however, no in-vivo data were presented to demonstrate improved efficacy.

PCT Application WO 96/10417 describes the co-administration of $Asp^{B28}$ human insulin and nicotinamide in order to achieve a rapid onset of action of the hypoglycaemic effect. The claimed nicotinamide concentration range was 0.01 to 1 M (0.1–12% w/w), but preferably from 0.05 to 0.5 M. The document gives evidence for faster absorption during an in-vivo study in pigs, however, a mechanism by which the improved absorption occurs is not addressed and, therefore, no generalisable teachings can be drawn from this document.

DESCRIPTION OF THE INVENTION

It has been found that when a non-ionic aromatic hydrotropic agent is added to aqueous solutions of a peptide drug, which is normally poorly soluble in aqueous physiological saline solution, its solubility is increased and the resulting pharmaceutical compositions also show excellent stability.

In particular, it has been found that when nicotinamide is added to a saline solution (0.9% NaCl) of antide, the molecule can promote the solubility of this drug. The final concentration of antide solubilised is dependent on the concentration of nicotinamide added and increases exponentially with increased nicotinamide concentration, as shown below. The solubility of the gonadotrophin releasing hormone antagonists is known to increase as the pH of the solution is reduced, however, the data reported here in the experimental section for antide show that the increased solubility is not due to a pH effect. In addition, it has been found that nicotinamide can also increase the solubility of antide in purely aqueous environments.

Therefore, the main object of the present invention is to provide a pharmaceutical composition comprising:
  a) a peptide poorly soluble in aqueous physiological saline solution, as active ingredient;
  b) a non-ionic aromatic hydrotropic pharmaceutically acceptable agent; and
  c) a physiological aqueous solution.

The peptide active ingredient can be an LHRH analogue or a growth hormone releasing factor (GRF) peptide. Preferably, the LHRH analogue is an antagonist. More preferably, it is antide, hGRF or PEG-conjugates thereof According to this invention the word "hGRF" is intended to cover any human GRF peptide, with particular reference to the 1–44, 1–40, 1–29 peptides and the corresponding amides thereof (containing —$NH_2$ at their end). They are all commercial compounds. The preferred hGRF is hGRF (1–29)—$NH_2$. The GRF peptide used in the Examples will be the commercial product specified in the "Materials" paragraph.

It has also been discovered that the addition of nicotinamide to aqueous solutions of hGRF can reduce the rate of deamidation of $Asn^8$ and of additional degradation products, not all of which have been identified at the present time. It is known that $Asn^8$ can degrade in aqueous solution to form the following degradation products: $\alpha$-$Asp^8$, $\beta$-$Asp^8$ and succinimidyl-$Asn^8$.

It has also been discovered that GRF can be dissolved in non-aqueous solvents and by the consequent reduction of the activity of water in the solution, deamidation at position $Asn^8$ is prevented. When the GRF is dissolved in propylene glycol (PG), it was found that alternative (not fully characterised) degradation pathways occur. It has also been found that by incorporating nicotinamide into non-aqueous solution such as PG, the rate of formation of some of these additional degradation products is reduced.

A non-limiting list of suitable pharmaceutically acceptable non-ionic aromatic hydrotropic agents comprises: nicotinamide, nicotinic acid, benzoic acid, salicylic acid, gentisic acid, ascorbic acid, histidine, tryptophan, phenylalanine, tyrosine, cresol, phenol, xanthines, pyridoxine, folic acid, saccharin. Non-ionic derivatives of any of the above compounds would also be applicable for the purposes of this invention. Nicotinamide is the preferred one.

Nicotinamide is a commonly used source of vitamin B in pharmaceutical products and is administered mainly by the oral route, but also by injection. Doses of up to 500 mg daily (in divided doses) have been recommended, e.g. see Martindale.

The physiological aqueous solution can be isotonic saline or phosphate buffered saline or any suitable solution containing inorganic salts at the same tonicity as the physiological medium.

The compositions of the present invention can be suitable for any administration route, such as oral, parenteral, nasal or pulmonary administration. They can be in liquid form, as well as, in solid form as an intimate mixture (for example following spray drying, lyophilisation, etc.). They can be, for example (but not limited to), in a solid dosage form, such as a gelatin capsule for oral administration, or formulated for nasal or pulmonary inhalation. Other pharmaceutically acceptable dosage forms could be employed such as suspension, emulsion, microemulsion, micronised powder, solution, suppository, pessary, microsphere, nanosphere, implant, etc, whereby the absorption or stability of the peptide drug is improved by the combination with the non-ionic hydrotropic agent. Oral microemulsions are particularly preferred administrations forms.

Therefore, the compositions of the present invention can also be lyophilized and reconstitutable and further comprise one or more stabilising agents, as well as one or more pharmaceutically acceptable excipients.

| antide or hGRF | 0.1–20.0 mg |
|---|---|
| nicotinamide | 10–300 mg |
| propylene glycol | 0–800 mg |
| Aqueous phase, q.s. | 1.0 ml. |

The term "peptide", as used in this application, means any compound made up of two or more amino acids. In it, the amino ($NH_2$) group of one amino acid joins the carboxyl (COOH) group of another, forming a peptide bond. Such amino acids can be naturally occurring, chemically synthesised or modified. The peptides according to the invention have generally up to 100 amino acids, preferably up to 50, more preferably up to 20.

The wording "poorly soluble in aqueous physiological saline solution", as used in the present application, means that in such a solution, at room temperature without the addition of acids or bases, the peptide shows a solubility<1 mg/ml and/or that the solubility in aqueous physiological saline solution is one order of magnitude lower than the solubility in water alone under the same conditions.

The invention will now be described by means of the following Examples, which should not be construed as in any way limiting the present invention. The Examples will refer to the Figure specified here below.

EXAMPLES

Materials
  Antide bulk (Bachem), batches 8901 and 9001
  hGRF(1–29)-$NH_2$ (Bachem), batches 1299201 and 1299202
  Dulbecco's phosphate buffered saline (Sigma, D-8537)
  Histidine hydrochloride (Merck. 1.04351 —Biochemistry grade),
  Nicotinamide (Fluka, 72345), USP grade,
  Phenylalanine (Merck, 7256)—Biochemistry grade.
  Sodium benzoate (Merck, 6290), Ph.Eur/NF grade.
  Sodium salicylate (Sigma, S-3007)—General Purpose Reagent, 35H1207.
  Thiamine hydrochloride (Merck 8181)—Biochemistry grade.
  Rubber stoppers, butyl rubber (Pharmagummi, art. 1779 W1816 grey)
  3 mil vials DIN2R glass type I (Nuova Ompi)
  All the other reagents used were "Analytical grade", unless otherwise specified.
Equipment
  The following equipment was used:
  Merck Hitachi HPLC system (L-6200 Pump, L-4250 Detector, AS-2000A Autosampler, Compaq PC, HPLC-Manager 2000 software)
  Waters HPLC system (626 Pump, 600S Controller, 994 Detector, 717 Autosampler, NEC PC, Maxima Baseline software)
  Freeze-dryer (Edwards, Lyoflex mod. 06 and mod. 04)
Analytical Method for Antide
  RP-HPLC gradient elution, C-18 (e.g. Vydac 218 TP54, 250×4.6 mm) column. UV detection at 215 nm, injection volume 15 µl, mobile phase A: pH 4.5 phosphate buffer (0.1 M), mobile phase B: acetonitrile, flow rate=1.0 ml/min, runtime=23 min. External standard solution concentrations of 100 µg/ml were injected during analysis. The gradient was: 77% A, 23% B to 52% A, 48% B over 30 min.

Analytical Method for hGRF
  A RP-HPLC method has been developed for the analysis of GRF(1–29)—$NH_2$ which is capable of differentiating the following degradation products:
  Oxidised: at $Met^{27}$
  Free acid: GRF(1–29)OH
  Desamido: $\alpha$-$Asp^8$, $\beta$-$Asp^8$ and succinimidyl-$Asn^8$
  Acetylated: acetyl $Tyr^1$
  Isomerised: $\beta$-$Asp^3$ and succinimidyl-$Asp^3$
  Truncated: hGRF(4–29)—$NH_2$, GRF(9–29)—$NH_2$.

This method has been used to determine the chemical purity of a number of solutions of hGRF, during storage at 4° and 40° C. as demonstrated in the following tables.

Conditions were similar to those for antide, using a mobile phase composed of $ACN/H_2O$ and with TFA in place of phosphate buffer. The gradient operated over a period of 60 minutes, with a total run time of 80 minutes.

Antide Stability in Aqueous Solutions
  Preliminary stability testing of 0.1 mg/ml antide solutions at −20° C., 4° C., 25° C. and 40° C. was performed to evaluate their stability at pH 2, 3 and 4. The solutions at 0.1 mg/ml were prepared dissolving antide in water and adjusting the pH using 0.01 M hydrochloric acid.

hGRF Stability in Aqueous Solutions
  Stability testing of 2.0 mg/ml, 5.0 mg/ml and 10.0 mg/ml hGRF aqueous solutions at 4° C. and 40° C., incorporating nicotinamide was performed to evaluate their stability at pH 7.5. The effect of the addition of propylene glycol has also been evaluated.

Solubilisation Studies for Antide
  Solubilisation studies were carried out to study the effect of:
    pH (solutions were acidified with either acetic acid or hydrochloric acid)
    hydrotropic agents (nicotinamide, sodium saccharin, sodium salicylate, sodium benzoate, histidine hydrochloride, thiamine hydrochloride, phenylalanine).

Saline used in these studies corresponds to 0.9% sodium chloride solution.

Based on the results of previous studies, excess antide was added to the test solution and observed visually to evaluate the solubility following equilibration overnight at 25° C. Following the visual analysis, a number of solutions were selected for further quantitative determination of the solubility by filtration (0.45 µm filters) and appropriate dilution using the RP-HPLC method described above.

Solubilisation Studies for hGRF
  Solubilisation studies were carried out to study the effect of saline and pH 7 phosphate buffer on the solubility of hGRF.
  Qunatitation of the amount of hGRF dissolved was performed by filtration of the equilibrated solution through a 0.45 µm filter prior to dilution and analysis by HPLC.

Manufacturing of Antide Freeze Dried Formulation
  50 vials of antide/nicotinamide freeze-dried product are manufactured as follows:
  1) weigh 0.7 g antide acetate (expressed as dry powder), weigh 3.5 g mannitol and add about 50 ml water for injectables (WFI)
  2) bring both materials into solution by gentle stirring
  3) bring to final weight of 70 g with WFI
  4) fill the vials with 1 ml of solution
  5) freeze-drying cycle:
    Load the product at room temperature.

Bring the product to −40° C. and maintain for 1.5 hours, then apply vacuum.

Perform primary drying for 2 hours.

Raise the shelf temperature to +20° C. and maintain for 16 hours.

Raise the shelf temperature to +40° C. and maintain for 5 hours to complete.

Results and Discussion

Antide Stability in Aqueous Solutions

Three month stability testing of 0.1 mg/ml antide solutions at pH 2, 3 and 4, adjusted using diluted hydrochloric acid and stored at −20° C., +4° C., +25° C. and +40° C. is shown in Tables 1 & 2. The percentage of degradation increased as the pH decreased as defined by the purity values observed. It was also seen that storage at −20° C. negatively affected the stability of the product when the pH was lower than 4.

Solubilisation Studies for Antide

Effect of pH

Tables 3 to 7 summarise the observations collected in order to obtain information on the solubility behaviour of antide in water for injectables (WFI), WFI acidified by HCl or acetic acid, saline and saline acidified by acetic acid. In agreement with previous studies, the solubility of antide increased as the pH decreased.

In Table 3, the natural pH of antide acetate in solution is from 4.4 to 5.0, depending on the amount dissolved. Antide could be dissolved easily in water at a concentration of 1.0 mg/ml, however, without further acidification the solubility limit was found to be 8.1 mg/ml. The pH was not measured when the solution had gelled.

When antide was added at 50 mg/ml to water adjusted to pH 3.0 with hydrochloric acid, a gel formed, indicating partial solubility. On the basis of these results, it would be necessary to add further acid in order to fully solubilise a solution at this concentration.

Tables 4 and 5 show that significant amounts of acetic acid did not effectively solubilise antide in water. The addition of 2% acetic acid in water which equates to 0.33 M solution, (deemed too concentrated for injectable purposes) was found to effectively solubilise between 10 and 20 mg/ml of antide.

The addition of 5 mg/ml antide to 1% acetic acid gave a solution of pH 3.12 in the presence of saline. The solution remained opalescent, indicating that the drug solubility was less than 5 mg/ml, the exact amount was not quantified (Table 6).

Table 7 shows that antide at a concentration of 10 mg/ml in saline is not soluble at a pH of 3.0 or 4.6, using 4% acetic acid to achieve the reduction in pH. The pH was measured when the solution was prepared, after which the gel gradually formed indicating the partial solubility of the drug. At pH 3.0 the solubility of the drug in saline solution was found to be 2.2 mg/ml, compared to the value of 0.025 mg/ml at the natural pH of 5.04 for this solution.

Effect of Hydrotropic Solubilising Agents on Antide Solubility

The effect of different hydrotropic agents (1.5% & 15% w/w) in saline solutions was also evaluated and is described in Tables 8 and 9. Nicotinamide and thiamine hydrochloride proved to be the most effective solubilising agents.

Table 8 shows the effect of low concentrations (1.5% w/w) of the hydrotropic agents selected on the pH of the solution as measured before drug addition, however, they were not effective in solubilising antide at a level of 10 mg/ml in saline.

The experiment described in Table 8 was repeated using a lower concentration of drug and a higher concentration of hydrotropic agent as described in Table 9. On quantifying the amount of antide dissolved, it was found that nicotinamide was a very good solubilising agent for antide, with 3.3 mg/ml dissolved in 15% w/w nicotinamide/saline solution at pH 5.8. Thiamine hydrochloride also solubilised significant amounts of antide in saline, with 3.0 mg/ml dissolved in 15% w/w saline solution. In this case, however, the acidification caused by the acid salt of thiamine caused a substantial reduction of pH to 3.3 and the solubilising power was largely due to the acidity of this solution. Ionic hydrotropic agents did not result in good solubilisation of antide in saline.

Nicotinamide

Further investigations were carried out to confirm the solubilising effect of nicotinamide on antide in saline solution and to establish the most effective concentration to use. The effect of the concentration of nicotinamide on antide solubility is shown in Table 10, where it was found that 20% nicotinamide in saline allows the solubilisation of 8.5 mg/ml antide.

Figure 1:
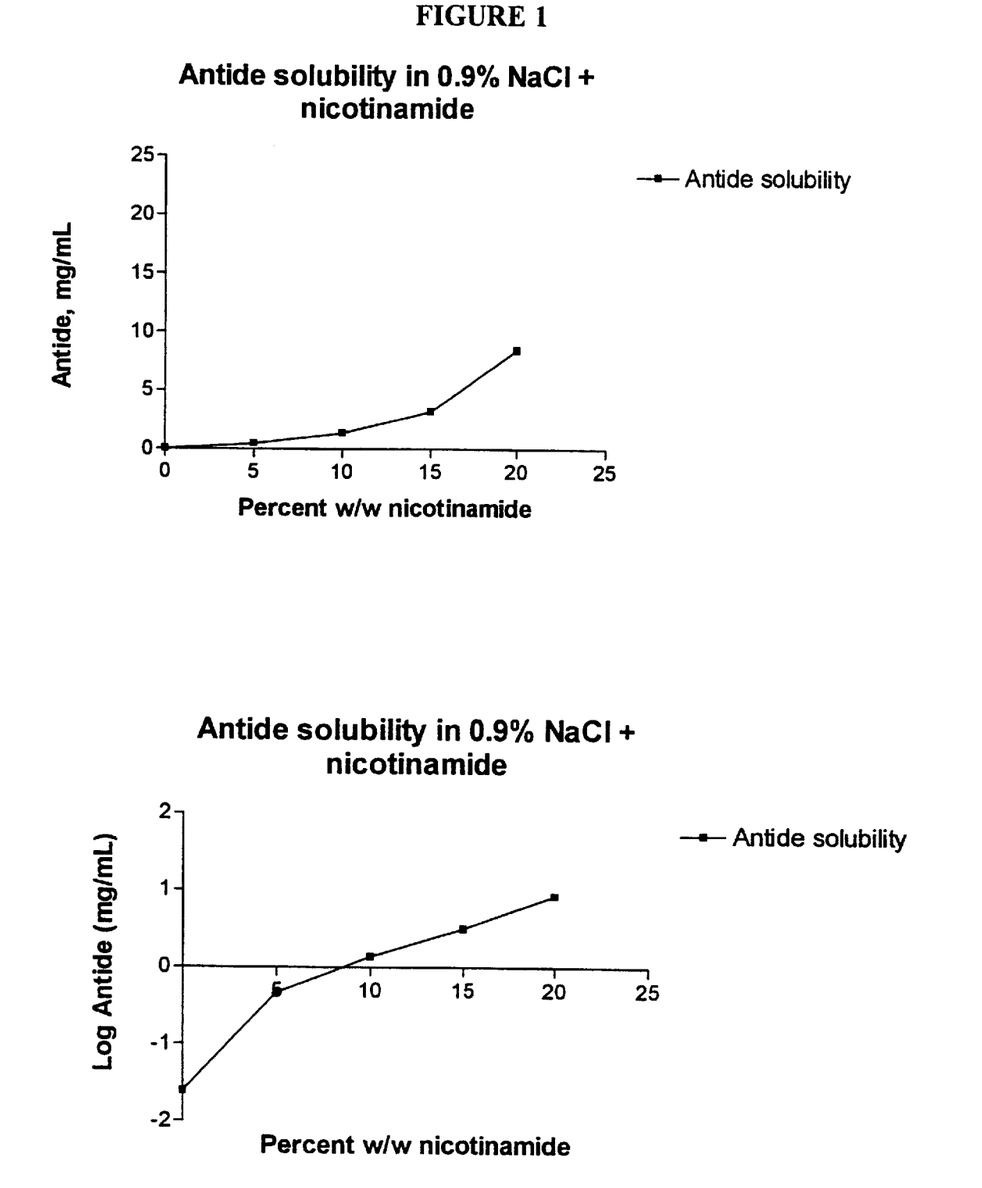
FIG. 1: The antide solubility in 0.9% NaCl solution versus nicotinamide concentration is reported. The semi logarithmic plot shows that the solubility of antide bears a logarithmic relationship with the concentration of nicotinamide present. The linear nature of this profile is important, as it allows dilution effects to be considered accurately and also shows that an equilibrium solubility has been reached for the drug in these solutions.

These results are shown graphically in FIG. 1. The semi logarithmic plot shows that the solubility of antide bears a logarithmic relationship with the concentration of nicotinamide present. The linear nature of this profile is important as it allows dilution effects to be considered accurately and also shows that an equilibrium solubility has been reached for the drug in these solutions.

Since nicotinamide proved to be a very good solubilising agent for antide, a further study was undertaken to verify the chemical compatibility between nicotinamide and antide. Four formulations of antide and nicotinamide at different concentration ratios and adjusted to pH 5 were prepared and tested over 3 months at +40° C., +25° C. and +4° C. The stability data are reported in Table 11.

An increased viscosity with precipitate formation was observed in the formulation containing 10 mg/ml antide and 5% nicotinamide after 1 week at +40° C. and +25° C.; no change was observed in the samples stored at +4° C. This indicated that the solubility of antide in nicotinamide/saline solutions diminished as the temperature rose. No chemical degradation was observed in the formulations after 3 months, indicating that no chemical incompatibility existed between the two substances at the investigated ratios. Chromatographic traces of antide were identical to those of the standard, with the addition of the early eluting nicotinamide peak which appeared at a retention time of 3.2 minutes.

The amounts of nicotinamide required to solubilise antide following injection may be greater than the isotonic concentration of nicotinamide which is 4.5%. Therefore, following injection at an extravascular site, the body fluids would re-equilibrate to adjust the osmotic balance, resulting in a dilution of the solubilising agent. In an effort to simulate the potential dilution of an injected formulation that could occur, the effect of diluting formulations containing antide and nicotinamide in phosphate buffered solution (PBS) was studied by the following in-vitro experiments. The dilutions were made to bring the nicotinamide concentration to 5% following the addition of PBS. Solutions of antide at concentrations from 1 to 5 mg/ml were prepared in 15% nicotinamide/WFI, followed by dilution in PBS by a factor of 3.Observations were performed over a period of 3 hours, with the effect of the dilution in PBS shown in Table 12.

The results are in good agreement with the measured solubility of antide in these systems, reported in Table 10 where a solution of 5% nicotinamide in saline can solubilise about 0.5 mg/ml of antide. The data shows that it is possible to produce a slightly supersaturated solution of antide in the body fluids by preparing, e.g. a 2 mg/ml solution of antide in 15% nicotinamide. On dilution to 5% this would contain 0.67 mg/ml of antide which remained in solution during the studies reported above.

Therefore, suitable formulations containing for example 15% nicotinamide and 2 mg/ml of antide or 5% nicotinamide and 0.5 mg/ml of antide may reduce precipitation at the injection site after administration. Other suitable formulations, such as those described above, can be determined from the solubility profiles in FIG. 1 and are preferred in accordance with this invention.

As a result of the Examples above, antide can be effectively solubilised by a number of agents which are non-ionic aromatic hydrotropic compounds, while the addition of ionised species reduces the aqueous solubility. Antide solubility is shown to increase with decreasing pH, while the chemical stability of antide decreases as the pH is reduced below the value of pH 4.

It is also found that antide remains chemically stable in the presence of nicotinamide.

Solubilisation Studies for hGRF

The solubility of hGRF was measured at 25° C. in water versus saline (stored for one week to reach equilibrium) and PBS stored for 5 days. The solubilities were

| | |
|---|---|
| WFI | >1 mg/ml |
| 0.9% NaCl | 0.042 mg/ml |
| PBS | 0.032 mg/ml |

After storage at 40° C. for one week, the following solubilities were observed:

| | |
|---|---|
| 0.9% NaCl | 0.097 mg/ml |
| 0.9% NaCl + 5% nicotinatnide | 0.875 mg/ml. | hGRF solutions (5 and 20 mg/ml) were prepared in water adjusted to pH 3.0 and 5% or 20% nicotinamide added. By increasing the pH, the point of hGRF precipitation was determined. The results demonstrate the ability of nicotinamide to solubilise hGRF even at high pH. The results are reported in Table 13.

hGRF Stability in Aqueous Solutions

By incorporating nicotinamide into aqueous solutions of hGRF, it has been discovered that this agent also has the ability to dramatically reduce the chemical degradation of this peptide. GRF is known to degrade rapidly through deamidation in aqueous solution, the rate of which is increased by increasing the pH above the 4–5 region. Aqueous solutions of hGRF were prepared in water adjusted to pH 7.5, containing either 0, 5 or 20% nicotinamide and stored for up to 12 weeks at 4° and 40° C.

The data presented in Tables 14 and 15 show that the rate of deamidation is substantially reduced by the presence of nicotinamide, particularly the rate of deamidation at the asparagine at position 8 in hGRF, with solutions more stable at the lower temperature.

Since deamidation occurs in solution, the activity of water is an important factor governing the rate of degradation. Therefore, since hGRF is soluble in propylene glycol, the stability of hGRF in solution in this solvent was studied in order to understand the effect on deamidation reactions.

The data presented in Tables 16 and 17 demonstrate that degradation via deamidation at the asparagine at position 8 was reduced to a very low level in this solution. The data also show that hGRF dissolved in propylene glycol shows substantial degradation via routes which have not as yet been fully determined, with numerous new degradation products forming as peaks eluting after the main peak for hGRF under the chromatographic conditions employed.

It can be seen clearly from the data that the addition of nicotinamide to the solution of hGRF in propylene glycol causes a substantial reduction in the level of these degradation products. The rates of degradation were again affected by temperature with the solutions at 4° C. being more stable than at 40° C.

To evaluate the effect of combining both nicotinamide and propylene glycol in an aqueous solution of hGRF, 10 mg of hGRF was dissolved in a solution containing 60% propylene glycol and 20% nicotinamide, made up to volume with water adjusted to pH 7.5.

The data presented in Tables 18, 19 and 20 demonstrate that degradation via deamidation at the asparagine at position 8 was reduced to a very low level in this solution and at 4° C. the rate of degradation was sufficiently low to be considered for pharmaceutical applications.

These data show the stabilisation of aqueous solutions of hGRF by the use of nicotinamide and incorporating propylene glycol. It is considered that for different pharmaceutical applications the composition could be optimised or that other non-aqueous solvents could be employed to reduce the activity of water.

However, the stabilising actions of nicotinamide are necessary for effective pharmaceutical performance.

TABLE 1

Stability of 0.1 mg/ml antide solutions at pH 2, 3 and 4; Temp = +4° and −20° C.

| | | | −20° C. | | +4° C. | |
|---|---|---|---|---|---|---|
| Formuln. | Test | T = 0 | 5W | 5W | 12W | |
| pH = 2 | Purity (%) | 99.60 | 87.50 | 98.80 | 98.20 | |
| pH = 3 | Purity (%) | 99.60 | 93.50 | 99.40 | 99.10 | |
| pH = 4 | Purity (%) | 99.50 | 99.30 | 99.2 | 99.20 | |

TABLE 2

Stability of 0.1 mg/ml antide solutions at pH 2, 3 and 4; Temp = +25° and +40° C.

| | | | +25° C. | | +40° C. | |
|---|---|---|---|---|---|---|
| Formuln. | Test | T = 0 | 5W | 12W | 5W | 12W |
| pH = 2 | purity (%) | 99.6 | 95.8 | 92.0 | 83.4 | 65.0 |
| pH = 3 | Purity (%) | 99.6 | 99.0 | 98.8 | 97.7 | 95.6 |
| pH = 4 | Purity (%) | 99.5 | 99.6 | 99.4 | 99.4 | 99.1 |

TABLE 3

| antide solubility in WFI | | | |
|---|---|---|---|
| antide (nominal amount added, mg/ml) | Appearance | pH | Solubility (mg/ml) |
| 50 | gel | ND | ND |
| 10 | opalescent | 4.40 | 8.13 |
| 1 | clear | 5.00 | 1.00 |

TABLE 4 antide solubility in WFI + 4% acetic acid

| antide (nominal amount added, mg/ml) | Appearance | pH |
|---|---|---|
| 100 | gel | ND |
| 50 | gel | ND |
| 33 | gel | ND |
| 25 | opalescent | 3.18 |

TABLE 5 antide solubility in WFI + 2% acetic acid

| antide (nominal amount added, mg/ml) | Appearance | pH |
|---|---|---|
| 40 | gel | ND |
| 20 | opalescent | 3.31 |
| 10 | clear | 3.31 |

TABLE 6 antide solubility in saline + 1% acetic acid

| antide (nominal amount added, mg/ml) | Appearance | pH |
|---|---|---|
| 10 | gel | ND |
| 5 | opalescent | 3.12 |

TABLE 7

Effect of pH on antide solubility in saline

| antide (nominal amount added, mg/ml) | pH | Appearance | Solubility (mg/ml) |
|---|---|---|---|
| 1 | 5.04 | opalescent | 0.025 |
| 10 | 4.61 | gel | ND |
| 10 | 3.01 | opalescent | 2.23 |

TABLE 8

Effect of 1.5% hydrotropic agents on antide solubility in saline

| antide (nominal amount added, mg/ml) | Hydrotropic agent | pH | Appearance | Solubility (mg/ml) |
|---|---|---|---|---|
| 10 | nicotinamide | 4.89 | gel | ND |
| 10 | saccharin | 4.61 | gel | ND |
| 10 | sodium salicylate | 5.08 | gel | ND |
| 10 | thiamine hydrochloride | 3.94 | gel | ND |

TABLE 9

Effect of 15% hydrotropic agents on antide solubility in saline

| antide (nominal amount added, mg/ml) | Hydrotropic agent | pH | Appearance | Solubility (mg/ml) |
|---|---|---|---|---|
| 5 | nicotinamide | 5.79 | opalescent | 3.32 |
| 5 | sodium salicylate | 5.81 | opalescent | 0.21 |
| 5 | thiamine hydrochloride | 3.30 | opalescent | 3.01 |
| 5 | sodium benzoate | 6.69 | opalescent | 0.072 |
| 5 | histidine hydrochloride (5%) | 4.17 | opalescent | 0.076 |
| 5 | phenylalanine (1.7%) | 4.59 | opalescent | 0.066 |

TABLE 10

Effect of nicotinamide concentration on antide solubility in saline

| antide (nominal amount added, mg/ml) | Nicotinamide (%) | pH | Appearance | Solubility (mg/ml) |
|---|---|---|---|---|
| 1 | 5 | ND | opalescent | 0.47 |
| 5 | 10 | 5.68 | opalescent | 1.40 |
| 5 | 15 | 5.76 | opalescent | 3.23 |
| 10 | 20 | 5.64 | opalescent | 8.49 |

TABLE 11

Stability of nicotinamide/antide formulations at 4°, 25° and 40° C.

| antide (mg/ml) | Nicotinamide (%) | T = 0 | +4° C. | | | +25° C. | | | +40° C. | | |
|---|---|---|---|---|---|---|---|---|---|---|---|
| | | | 1W | 4W | 12W | 1W | 4W | 12W | 1W | 4W | 12W |
| 1 | 5 | 1.0 | ND | 0.9 | 1.0 | 0.9 | 0.9 | 1.0 | 1.0 | 0.9 | 1.0 |
| 1 | 25 | 1.0 | ND | 1.0 | 1.1 | 1.0 | 1.0 | 1.1 | 1.0 | 1.0 | 1.1 |
| 10 | 5 | 9.7 | 10.3 | 10.0 | 10.5 | gel | gel | gel | gel | gel | gel |
| 10 | 25 | 9.8 | ND | 10.1 | ND | 9.8 | 9.5 | 11.1 | 10.7 | 9.4 | 10.2 |

TABLE 12

Effect of 1:3 dilution of antide/15% w/w nicotinamide solutions in PBS

| Time (min) | Ant. 5 mg/ml nic. 15% Dilution 1:3 (PBS) | Ant. 4 mg/ml nic. 15% Dilution 1:3 (PBS) | Ant. 3 mg/ml nic. 15% Dilution 1:3 (PBS) | Ant. 2 mg/ml nic. 15% Dilution 1:3 (PBS) | Ant. 1 mg/ml nic. 15% Dilution 1:3 (PBS) |
|---|---|---|---|---|---|
| 0 | opalescent | opalescent | clear | clear | clear |
| 5 | precipitate | precipitate | clear | clear | clear |
| 15 | precipitate | precipitate | opalescent | clear | clear |
| 30 | precipitate | precipitate | precipitate | clear | clear |
| 60 | precipitate | precipitate | precipitate | clear | clear |
| 120 | precipitate | precipitate | precipitate | clear | clear |
| 180 | precipitate | precipitate | precipitate | clear | clear |

TABLE 13 hGRF solubility in aqueous nicotinamide solutions

| Solutions | Initial pH | Precipitation point (pH) |
|---|---|---|
| GRF (5 mg/ml in H$_2$O at pH 3) | 4.93 | 10.09 |
| GRF (20 mg/ml in H$_2$O at pH 3) | 4.94 | 7.20 |
| GRF (5 mg/ml in H$_2$O at pH 3 + 5% nicotinamide) | 5.65 | 12.28 |
| GRF (20 mg/ml in H$_2$O at pH 3 + 5% nicotinamide) | 5.30 | 10.10 |
| GRF (5 mg/ml in H$_2$O at pH 3 + 20% nicotinamide) | 6.76 | 12.01 |
| GRF (20 mg/ml in H$_2$O at pH 3 + 20% nicotinamide) | 5.52 | 12.38 |

TABLE 14

Stability at +40° C. for GRF (2 mg/ml) + nicotinamide solutions adjusted to pH 7.5

| 1 WEEK | Chromatographic peak areas (%). In order of elution. | | | | | | |
|---|---|---|---|---|---|---|---|
| % Nicotinamide | rtr = 0.76 | β-Asp8 | β-Asp3 | Succ-N8 ? | GRF1-29 | Succ-D3 | + Asp8 |
| 0 | 0.8 | 16.7 | 3.8 | 0.3 | 68.0 | nr | 5.2 |
| 5 | 0.5 | 13.4 | 3.5 | 0.3 | 73.9 | 0.9 | 3.9 |
| 20 | 0.5 | 11.5 | 3.6 | 0.3 | 77.1 | 0.9 | 3.1 |
| 4 WEEKS | Chromatographic peak areas (%). | | | | | | |
| % Nicotinamide | rtr = 0.76 | β-Asp8 | β-Asp3 | Succ-N8 ? | GRF1-29 | Succ-D3 ? | + Asp8 |
| 0 | 6.2 | 37.8 | 5.7 | 2.7 | 22.2 | 2.9 | 10.4 |
| 5 | 4.9 | 33.3 | 6.4 | 1.9 | 31.5 | 2.4 | 9.0 |
| 20 | 4.2 | 28.6 | 7.5 | 2.1 | 39.5 | 2.6 | 7.6 |

TABLE 15

Stability at +4° C. for hGRF (2 mg/ml) + nicotinamide solutions adjusted to pH 7.5

| | Chromatographic peak areas (%). In order of elution. | | | | | | |
|---|---|---|---|---|---|---|---|
| % Nicotinamide | 4-29 | β-Asp$^8$ | β-Asp$^3$ | Succ-N8 ? | GRF1-29 | Succ-D3 ? + Asp$^8$ | |
| Time zero * | 0.1 | 0.2 | 0 | 0.3 | 97.6 | nr | 0.6 |
| 4 WEEKS | | | | | | | |
| 0 | 0 | 1.4 | 0.1 | 0.1 | 95.4 | nr | 0.8 |
| 5 | 0 | 0.9 | 0.1 | 0 | 96.8 | nr | 0.6 |
| 20 | 0 | 0.8 | 0.1 | 0 | 97.4 | nr | 0.6 |
| 8 WEEKS | | | | | | | |
| 0 | 0 | 2.4 | 0.2 | 0.1 | 93.2 | nr | 1.1 |
| 5 | 0 | 1.5 | 0.2 | 0.1 | 95.8 | nr | 0.9 |
| 20 | 0 | 1.4 | 0.2 | 0.1 | 96.3 | nr | 0.8 |
| 12 WEEKS | | | | | | | |
| 0 | 1.06 | 3.39 | 0.27 | 0.07 | 89.9 | nr | 1.29 |
| 5 | 0.28 | 2.12 | 0.26 | 0.11 | 94.0 | nr | 0.97 |
| 20 | 0.15 | 1.95 | 0.26 | 0.10 | 95.1 | nr | 0.97 |

Legend (for the abbreviations in the Tables 14–15):
nr = not resolved. The Succ-D3 + Asp$^8$ may elute as an overlapping peak
? = further characterisation is necessary to confirm peak identity
rtr = retention time ratio

TABLE 16

Stability at +4° C. for hGRF (5 mg/ml) in propylene glycol + nicotinamide solutions adjusted to pH 7.5

| 1 WEEK 4° C. | Chromatographic peak areas (%). In order of elution. | | | | | | |
|---|---|---|---|---|---|---|---|
| % Nicotinamide | Met-Ox | β-Asp$^8$ | Succ-N8 | 1-29OH | GRF1-29 | Succ-D3 + Asp$^8$ | rtr 1.07 |
| bulk 1299201 | 0.04 | 0 | 0.6 | 0.3 | 97.7 | 0.4 | 0.4 | 0 |
| 0 | 0.2 | 0 | 0.2 | 0.4 | 95.4 | 0.5 | 1.0 | — |
| 20 | 0.3 | 0 | 0.4 | 0.4 | 97.5 | 0.4 | 0.7 | — |

| 1 WEEK 4° C. | Chromatographic peak areas (%). In order of elution. | | | | | | |
|---|---|---|---|---|---|---|---|
| (Continued) | rtr 1.08 | rtr 1.11 | rtr 1.13 | rtr 1.17 | rtr 1.18 | rtr 1.20 | rtr 1.23 | rtr 1.39 |
| 0 | 0.2 | 0.2 | 0.4 | — | — | 0.9 | 0.4 | 0.1 |
| 20 | — | — | — | — | 0.3 | 0.2 | — | 0.2 |

| 4 WEEKS 4° C. | Chromatographic peak areas (%). In order of elution. | | | | | | |
|---|---|---|---|---|---|---|---|
| % Nicotinamide | Met-Ox | β-Asp8 | Succ-N8 | 1-29OH | GRF1-29 | Succ-D3 + Asp8 | rtr 1.07 |
| 0 | 0.1 | 0 | 0.2 | 0.3 | 95.0 | 0.4 | 0.9 | 0.4 |
| 20 | 0.4 | 0 | 0.3 | 0.3 | 97.1 | 0.4 | 1.0 | 0.1 |

| 4 WEEKS 4° C. | Chromatographic peak areas (%). In order of elution. | | | | | | |
|---|---|---|---|---|---|---|---|
| (Continued) | rtr 1.08 | rtr 1.11 | rtr 1.13 | rtr 1.17 | rtr 1.18 | rtr 1.20 | rtr 1.23 | rtr 1.36 |
| 0 | 0.2 | 0.6 | — | 1.6 | — | 0.3 | — | 0.1 |
| 20 | 0.1 | 0.1 | — | 0.1 | — | — | — | 0.1 |

| 8 WEEKS 4° C. | Chromatographic peak areas (%). In order of elution. | | | | | | |
|---|---|---|---|---|---|---|---|
| % Nicotinamide | Met-Ox | β-Asp$^8$ | Succ-N8 | 1-29OH | GRF1-29 | Succ-D3 + Asp$^8$ | rtr 1.07 |
| 0 | 0.3 | 0 | 0.2 | 0.3 | 92.2 | 1.2 | nr | 0.7 |
| 20 | 0.5 | 0 | 0.3 | 0.3 | 95.7 | 1.8 | nr | 0.1 |

TABLE 16-continued

Stability at +4° C. for hGRF (5 mg/ml) in propylene glycol + nicotinamide solutions adjusted to pH 7.5

| 8 WEEKS 4° C. | Chromatographic peak areas (%). In order of elution. | | | | | | |
|---|---|---|---|---|---|---|---|
| (Continued) | rtr 1.08 | rtr 1.10 | rtr 1.13 | rtr 1.17 | rtr 1.18 | rtr 1.20 | rtr 1.23 | rtr 1.36 |
| 0 | 0.5 | 0.9 | — | 2.6 | — | 0.5 | — | 0.1 |
| 20 | 0.1 | 0.1 | — | 0.2 | — | 0.1 | — | 0.1 |

TABLE 17

Stability at +40° C. for hGRF (5 mg/ml) in propylene glycol + nicotinamide solutions adjusted to pH 7.5

| 1 WEEK 4° C. | Chromatographic peak areas (%). In order of elution. | | | | | | |
|---|---|---|---|---|---|---|---|
| % Nicotinamide | Met-Ox | β-Asp$^8$ | Succ-N8 | 1-29OH | GRF1-29 | Succ-D3 + Asp$^8$ | rtr 1.07 |
| 0 | 0.3 | 0 | 0 | 0.1 | 82.9 | 1.1 | 1.2 | — |
| 20 | 1.6 | 0 | 0.3 | 0.2 | 88.0 | 1.3 | 1.6 | — |

| 1 WEEK 4° C. | Chromatographic peak areas (%). In order of elution. | | | | | | |
|---|---|---|---|---|---|---|---|
| (Continued) | rtr 1.08 | rtr 1.11 | rtr 1.13 | rtr 1.17 | rtr 1.18 | rtr 1.20 | rtr 1.23 | rtr 1.39 |
| 0 | 0.5 | 3.2 | 1.4 | 0.3 | 3.9 | 2.6 | 1.37 | 0.3 |
| 20 | 0.3 | 1.4 | 0.4 | 0 | 1.8 | 1.0 | 1.2 | 0 |

| 4 WEEKS 4° C. | Chromatographic peak areas (%). In order of elution. | | | | | | |
|---|---|---|---|---|---|---|---|
| % Nicotinamide | Met-Ox | β-Asp$^8$ | Succ-N8 | 1-29OH | GRF1-29 | Succ-D3 + Asp$^8$ | rtr 1.07 |
| 0 | 0.5 | 0 | 0 | 0 | 44.6 | 1.7 | 1.5 | 15.1 |
| 20 | 10.9 | 0.9 | 0 | 0.4 | 43.1 | 1.3 | 4.2 | 10.3 |

| 4 WEEKS 4° C. | Chromatographic peak areas (%). In order of elution. | | | | | | |
|---|---|---|---|---|---|---|---|
| (Continued) | rtr 1.08 | rtr 1.11 | rtr 1.13 | rtr 1.17 | rtr 1.18 | rtr 1.20 | rtr 1.23 | others |
| 0 | 15.3 | 8.4 | 1.4 | 3.4 | 1.4 | 2.1 | 1.2 | 3.4 (n = 8) |
| 20 | 8.9 | 4.3 | — | 2.5 | 2.0 | 2.0 | 0.9 | 8.4 (n = 7) | n = number of additional peaks occurring in chromatogram.

TABLE 18

Stability at +4° C. for hGRF (10 mg/ml) in 60% propylene glycole + 20% nicotinamide, 20% H$_2$O adjusted to pH 7.5

| | Chromatographic peak areas (%) | | | | | |
|---|---|---|---|---|---|---|
| | GRF 1-29 | Oxidation peaks (%) | 4-29 ? | β-Asp8 | β-Asp3 | Succ-N8 | Succ-D3 + Asp8 |
| RT Ratio | | 0.65–0.67 | 0.87 | 0.89 | 0.96 | 0.98 | 1.06 |
| T = 0 | 98.17 | 0.07–0.07 | — | 0.04 | — | 0.38 | 0.60 |
| 4 WEEKS | 97.97 | 0.06–0.07 | 0.03 | 0.03 | 0.03 | 0.28 | 0.84 |
| 8 WEEKS | 97.97 | 0.07–0.11 | 0.03 | 0.04 | 0.03 | 0.21 | 0.93 |
| 12 WEEKS | 97.62 | 0.07–0.07 | 0.08 | 0.06 | 0.09 | 0.16 | 0.93 |

TABLE 19

Stability at +25° C. for hGRF (10 mg/ml) in 60% propylene glycole + 20% nicotinamide, 20% H$_2$O adjusted to pH 7.5

| | GRF 1-29 | Oxidation peaks (%) | 4-29 ? | β-Asp8 | β-Asp3 | Succ-N8 | Succ-D3 + Asp8 |
|---|---|---|---|---|---|---|---|
| RT Ratio | | 0.65–0.67 | 0.87 | 0.89 | 0.96 | 0.98 | 1.06 |
| T = 0 | 98.17 | 0.07–0.07 | — | 0.04 | — | 0.38 | 0.60 |
| 4 WEEKS | 96.28 | 0.08–0.09 | 0.03 | 0.27 | 0.85 | 0.15 | 1.34 |
| 8 WEEKS | 93.69 | 0.12–0.15 | 0.03 | 0.47 | 2.34 | 0.08 | 1.57 |
| 12 WEEKS | 90.94 | 0.12–0.14 | 0.10 | 0.60 | 3.54 | 0.10 | 1.73 |

TABLE 20

Stability at +40° C. for hGRF (10 mg/ml) in 60% propylene glycole + 20% nicotinamide, 20% H$_2$O adjusted to pH 7.5

| | GRF 1-29 | Oxidation peaks (%) | rtr = 0.76 | β-Asp8 | β-Asp3 | Succ-N8 | Succ-D3 + Asp8 |
|---|---|---|---|---|---|---|---|
| T = 0 | 98.17 | 0.07–0.07 | — | 0.04 | — | 0.38 | 0.60 |
| 4 WEEKS | 84.06 | 0.15–0.16 | 0.22 | 1.75 | 8.59 | 0.10 | 2.18 |

(The Succ-D3 + Asp$^8$ may elute as a single unresolved peak)

References

Bongers, J., et al., *Int. J. Peptide. Protein Res.* 39, 364–374, 1992;
Cannon I. B., *J. Pharm. Sci.*, 84, 953–958, 1995;
Felix A. M. et al., *Peptides*, editors: Giralt E. and Andreu D., pp 732–733, Escom Publishers 1991;
Friedman, A. R. et al., *Int. J. Peptide. Protein Res.*, 37, 14–20, 1991;
Golightly L., et al., *Med. Toxicol.*, 3, 128–165, 1988;
Graham C. W. et al., *Anaesthesia & Analgesia*, 56, 409–13, 1977;
Maa Y. F. et al., *Int. J. Pharm.*, 140 (2): 155–168, 1996;
Rasool et al., *J. Pharm. Sci.*, 80(4), 387–393, 1991;
Sasaki H., *BioL. Pharm. Bull.* (Japan), 18/1, 169–171, 1995;
Serono Symposia USA, *Growth hormone secretagogiles*, Chapter 3, editors, B. B. Bercu & R.F. Walker, Springer-Verlag, New York, 1996;
Spiegel A. J. et al., *J. Pharm. Sci.*, 52, 917–927, 1963;
Wang Y-C. J. et al., *J. Parenter. Drug Assoc.*, 34, 452–462, 1980;
Yalkowsky S. H. et al., *Drug Int. Clin. Pharm.*, 11, 417–419, 1977;
Yalkowsky S. H. et al., *J. Pharm. Sci.*, 74, 416–412, 1986.

SEQUENCE LISTING

```
<160> NUMBER OF SEQ ID NOS:  1

<210> SEQ ID NO 1
<211> LENGTH: 10
<212> TYPE: PRT
<213> ORGANISM: Homo sapiens
<220> FEATURE:
<221> NAME/KEY: UNSURE
<222> LOCATION: (1)..(10)
<223> OTHER INFORMATION: Luteinising hormone releasing hormone

<400> SEQUENCE: 1

Glu His Trp Ser Tyr Gly Leu Arg Pro Gly
  1               5                  10
```

Jain N. K. et al., *The Eastern Pharmacist*, November, 51–54, 1986 Physicians Desk Reference, Librium monograph, 47th Edition, 1993;
Leone Bay A, et al., *J. Med Chem.*, 39(13), 2571–2578, 1996;

What is claimed is:

1. A pharmaceutical composition comprising:
   a) an LHRH peptide agonist, an LHRH peptide antagonist or a growth hormone releasing factor peptide as active ingredient;

b) nicotinamide; and c) a physiological aqueous solution.

2. The pharmaceutical composition according to claim 1, wherein the active ingredient is an LHRH peptide antagonist.

3. The pharmaceutical composition according to claim 1, wherein the active ingredient is antide (LHRH peptide antagonist) or human growth hormone releasing factor peptide.

4. The pharmaceutical composition according to claim 1, which is lyophilised and reconstitutable and further comprises stabilizer agents.

5. The pharmaceutical composition according to any of the preceding claims, which further comprises propylene glycol.

6. The pharmaceutical composition of claim 1, which has the following composition ranges:

antide (LHRH peptide antagonist) or human growth hormone releasing factor peptide

| [hGRF] | 0.1–20.0 mg |
|---|---|
| nicotinamide | 10–300 mg |
| propylene glycol | 0–800 mg |
| Aqueous phase, q.s. | 1.0 ml. |

\* \* \* \* \*